United States Patent [19]

Kindt-Larsen et al.

[11] Patent Number: 4,910,259
[45] Date of Patent: Mar. 20, 1990

[54] BONE CEMENT

[75] Inventors: Ture Kindt-Larsen, Vedbaek; Lydia D. Thomsen, Allerød, both of Denmark

[73] Assignee: Wolff & Kaaber A/s, Farum, Denmark

[21] Appl. No.: 248,708

[22] Filed: Sep. 26, 1988

[51] Int. Cl.$^4$ ............................................ C08F 265/06
[52] U.S. Cl. ..................... 525/259; 525/265; 525/289; 525/297; 525/937; 523/116; 523/117
[58] Field of Search ............... 523/116, 117; 525/289, 525/297, 937, 259, 265

[56] References Cited

U.S. PATENT DOCUMENTS

| | | | |
|---|---|---|---|
| 4,433,958 | 2/1984 | Fellman | 523/116 |
| 4,486,179 | 12/1984 | Brauer | 523/116 |
| 4,490,497 | 12/1984 | Evrard | 523/116 |
| 4,670,480 | 6/1987 | Morrone | 523/116 |
| 4,791,150 | 12/1988 | Braden | 523/116 |

FOREIGN PATENT DOCUMENTS 1431211  4/1976  United Kingdom .

Primary Examiner—Lewis T. Jacobs
Assistant Examiner—David Buttner
Attorney, Agent, or Firm—Lawrence Rosen

[57] ABSTRACT

An acrylate based bone cement with well balanced low exotherm, low residual monomer, and high strength properties formulated from (1) a liquid component containing at least three different monomeric (meth)acrylates, e.g. a $C_1$–$C_2$ alkyl methacrylate, a straight or branched long chain (meth)acrylate having a molecular weight of at least 168, and a cyclic (meth)acrylate having a molecular weight of at least 168, and (2) a polymer powder component containing (meth)acrylate polymers or copolymers. The final bone cement may also contain conventional additives such as polymerization inhibitors, activators, crosslinkers, X-ray contrast material, polymerization initiators, antibiotics, antiseptics, and the like.

18 Claims, No Drawings

BONE CEMENT

FIELD OF THE INVENTION

The present invention relates to an improved bone cement or adhesive composition. More particularly, the invention pertains to an improved acrylic bone cement, which is especially useful for orthopedic implants.

BACKGROUND OF THE INVENTION

The introduction of bone cement in the 1960s was a major breakthrough in orthopedic surgery. It was possible thereafter for the surgeon to replace nearly any damaged joint with implants attached to the bone with cement that fills irregularities of the bone/implant interface and furthermore acts as a filler of larger spaces or voids. Recent estimates indicate that each year in industrialized countries there are 1,000 implants per one million inhabitants. These have mainly involved the implantation of artificial hip joints.

Although the initial results of such implants have been excellent, long term clinical studies have shown loosening of the implant with time. This occurs either at the interface between implant and cement or more commonly at the interface between cement and bone. After about 10 years of service, at least 20% of hip joint implants require revision, which generally involves the insertion of new components.

Such high replacement statistics have led to considerable work to improve implant designs and to improve the bone cements. The latter generally have been formulated from methylmethacrylate (MMA) monomer and polymethylmethacrylate (PMMA) powder. Commercially available bone cements have differed from each other in particle size and composition of the PMMA powder, concentrations of accelerators such as N,N-dimethyl-p-toluidine, or the use of special additives such a radiopaque or X-ray contrast agents, antibiotics, dyes and the like.

As is well documented in numerous medical studies as well as in the patent literature, the cement, which cures in vivo after insertion of the implant, gives rise to problems; the major problem is bone necrosis, often a much as 0.5 cm, caused by the high exotherm at the interface between cement and bone and release of monomeric methylmethacrylate. High exotherm, exceeding 70° C., results from the polymerization or curing taking place in the bone cement following admixing of the ingredients immediately preceding its use with the implant. Unreacted methylmethacrylate is the source of the released monomeric methacrylate, which is highly toxic to bone cells. Moreover, the literature indicated that monomeric methacrylate myy deleteriously affect local blood circulation as well as the blood pressure of the patient.

It also has been observed that with time a membrane is formed at the cement/bone interface. As the membrane increases in thickness the bone becomes thinner and loosening of the implant and secondary dysfunction is observed. Ultimately, revision surgery is required. Although the reasons for this membrane formation are not fully understood at this time, histologic examinations show unspecified inflammatory tissue and it is supposed that the long term release of monomeric methylmethacrylate as well as an accelerator such as N,N-dimethyl-p-toluidine stimulates the development and growth of the undesirable inflammatory membrane.

Set forth below are prior patents that reveal the development of acrylate bone cements, the disadvantages of such bone cement, and recent efforts to overcome these problems; a discussion of the most relevant patents follows:

U.S. PATENTS 3,468,977—Buckmann et al.
4,093,576—deWijn
4,268,639—Seidel et al.
4,341,691—Anuta
4,404,327—Crugnola et al.
4,490,497—Evrard et al.
4,552,906—Podszun et al.
4,588,583—Pietsch et al.

OVERSEAS PATENTS 1,431,211—United Kingdom
1,532,318—United Kingdom
0,218,471—EPA US. Pat. No. 4,093,576 (de Wijn) discloses acrylic bone cements made from polymer powder (PMMA) and liquid monomer mixed with an incompatible high viscosity aqueous gel. The gel is soluble in the body fluids and dissolves out after implanting. This leaves a porous structure in the cured cement and reduces the exotherm. In order to control porosity the liquid monomer should preferably contain up to 5% of a tertiary amine, 10–45% by weight of ethyl-, propyl-, butyl-, isopropyl-, isobutyl-, isopentyl- or pentylmethacrylate. The remaining monomer being MMA.

U.S. Pat. No. 4,404,327 (Crugnola et al) discloses orthopaedic acrylic based cements with increased toughness and resistance to fracture due to the rubbery nature of the included polyacrylate phase. The polymer powder component has glass transition temperature (Tg) below the body temperature (37° C.) and is embedded in the rigid glassy matrix of the polymerized liquid MMA monomer. The preferred rubbery polymer is poly-n-butylmethacrylate. The modulus of these cements are significantly reduced (3–5 times) compared with conventional cements based on PMMA powder.

U.S. Pat. No. 4,490,497 (Evrard et al) discloses compositions for acrylic based surgical cements with the aim of reducing exotherm temperature. The polymer powder comprises PMMA with particle size from 20 to 150 microns. The liquid contains at least 65% by weight of an acrylic monomer, preferably MMA, up to 35% by weight of an acrylic polymer and from 0.01 to 1% by weight of a chain stopping agent such as diunsaturated monocyclic terpenes and monounsaturated bicyclic terpenes.

U.S. Pat. No. 4,588,583 (Pietsch et al) discloses acrylic based surgical cements with reduced exotherm and residual monomer obtained by adding 1–15% by weight of a non-toxic, liquid, non-reactive plasticizer. Suggested plasticizers are saturated aliphatic esters with boiling points above 100° C., preferred esters contain one or more free hydroxyl-groups like triethylcitrate.

U.K Pat.No. BP 1,431,211 (Sulzer Bros.) discloses acrylic bone cements with reduced exotherm obtained by mixing the PMMA powder with a liquid comprising at least 50% MMA and between 10 and 45% of at least one $C_2$–$C_6$-alkyl methacrylate, preferably isobutylmethacrylate.

European Patent Application No. 0.218.471 (Bonar Cole) discloses an acrylic composition for forming a bone cement. The powder component comprising polyethylmethacrylate incorporating opacifier therein, and the monomer comprising n-butylmethacrylate (BMA). The use of BMA as liquid monomer instead of MMA reduces the loss of liquid monomer to an aqueous medium during polymerization, reduces the exotherm and reduces the modulus of elasticity (softer polymer).

It has been argued that some reduction in mechanical strength could be beneficial (Bonar Cole and Crugnola), but a reduction of more than 50% in comparison with the commercially available cements is considered risky as the major portion (about 80%) of the commercially available PMMA/MMA based cements function satisfactorily. It is noteworthy that no low strength cements have become commercially accepted so far, and despite the other numerous attempts to overcome the problems associated with conventional bone cement there has been little, if any, commercial acceptance of new proposals. It would be advantageous therefore to have available a bone cement that would not only overcome the known problems but would also, because of its outstanding properties, be commercially acceptable and consequently reduce substantially the number of revisions and replacements of implants that are so prevalent in this field after finite periods of time. These are the objects of the present invention.

SUMMARY OF THE INVENTION

In accordance with the present invention it has been found advantageous to use a combination of a poly(meth)acrylate powder component and a liquid monomeric acrlate component comprising at least three different monomeric (meth)acrylates. More particularly, the liquid component contains at least a $C_1$-$C_2$ alkyl methacrylate, a straight or branched chain (meth)acrylate having a molecular weight of at least 168, and a cyclic (meth)acrylate having a molecular weight of at least 168. One of the preferred liquid monomeric components comprises an admixture of methylmethacrylate, n-decylmethacrylate, and iso-bornylmethacrylate. The powder component may comprise acrylic polymers or copolymers with a glass transition temperature in the range of 37° to 90° C. such as poly(butylmethacrylate-co-methylmethacrylate). Mixtures of polymers and copolymers may also be utilized. When these components are employed the exotherm is substantially reduced along with a much lower residual monomer content, when compared with commercially available bone cements. The compressive strength and modulus are still close to (50%–95%) that of commercially available bone cements. Furthermore by using certain accelerators or special combinations of accelerators the amount needed to give the specified cure time can be low, which lead to minimized long term release of toxic toluidine derivatives. It is these characteristics that lead to the superior bone cement composition of the present invention upon mixing the powder components with the liquid component.

It will be further understood that both the liquid and powder components may contain the conventional additives in this field. Thus, for example, the powder component may contain minor amounts of an X-ray contrast material, polymerization initiators, antibiotic, antiseptics, and the like. The liquid component may contain crosslinking agents and minor amounts of polymerization inhibitors, activators, color agents, and the like.

DETAILED DESCRIPTION OF THE INVENTION AND THE PREFERRED EMBODIMENT

As discussed above, the bone cement of the invention is prepared by admixing particles of a polymeric powder component, namely polymers or copolymers of (meth)acrylate as well as mixtures thereof with a mixture of at least three liquid (meth)acrylate monomers.

One of the most important aspects of the present invention is the composition of the liquid monomeric component. More specifically, it will contain at least three distinct (meth)acrylate monomers. The three groups are listed below along with certain of the preferred materials:

(1) $C_1$-$C_2$ Alkyl methacrylates:
Methylmethacrylate
Ethylmethacrylate (2) Straight or branched long chain (meth)acrylates having a molecular weight of at least 168 and preferably 6 to 18 carbon atoms in the straight or branched chain substituents:
n-hexylmethacrylate
n-heptylmethacrylate
ethylhexylmethacrylate
n-decylmethacrylate
isodecylmethacrylate
lauric methacrylate
stearic methacrylate
polyethyleneglycolmethacrylate
polypropyleneglycolmethacrylate
ethyltriglycolmethacrylate (3) Cyclic (meth)acrylates having a molecular weight of at least 168 and preferably 6 to 18 carbon atoms in the cyclic substituents:
cyclohexymethacrylate
benzylmethacrylate
iso-bornylmethacrylate
adamantylmethacrylate
dicyclopentenyloxyethylmethacrylate
dicyclopentenylmethacrylate
dicyclopentenylacrylate
3,3,5-trimethylcyclohexylmethacrylate
4-tert-butylcyclohexylmethacrylate As noted above, the liquid component or phase may contain crosslinking agents and minor amounts of additives such as polymerization inhibitors, activators, and the like. The polymerization inhibitors may be hydroquinone, hydroquinonemonomethylether, ascorbic acid, mixtures thereof, and the like in amounts ranging from about 10 to 500 ppm, preferably 20 to 100 ppm w/w. The activator is employed in amounts ranging from 0.2 to 3.0% w/w, preferably 0.4 to 1.0%, and may be N,N-dimethyl-p-toluidine, N,N-hydroxypropyl-p-toluidine, N,N-dimethyl-p-aminophen ethanol, N,N,-diethyl-p-aminophenyl acetic acid, and the like. In accordance with a further feature of the present invention, it has been found helpful to use a combination of N,N-dimethyl-p-toluidine and N,N-hydroxypropyl-p-toluidine. Most preferably, the latter compound is used in greater proportions, e.g. 2 parts by weight for each part of N,N-dimethyl-p-toluidine. Useful crosslinking agents include:
Ethyleneglycol dimethacrylate
1,4-butanediol dimethacrylate
1,3-butanediol dimethacrylate
Triethyleneglycol dimethacrylate
Tetraethyleneglycol dimethacrylate Polyethyleneglycol-400 dimethacrylate
Neopentylglycol dimethacrylate
Bisphenol A dimethacrylate
Ethoxylated Bisphenol A dimethacrylate
Trimethylolpropane trimethacrylate
Tripropyleneglycol acrylate The powder component or phase comprises a (meth-)acrylate polymer, copolymer or a mixture of both. Illustrative materials include:
polyethylmethacrylate
polyisopropylmethacrylate
poly-sec-butylmethacrylate
poly-iso-butylmethacrylate
polycyclohexylmethacrylate
poly(butylmethacrylate-co-methylmethacrylate)
poly(ethylmethacrylate-co-methylmethacrylate)
poly(styrene-co-butylacrylate)
poly(ethylacrylate-co-methylmethacrylate)

The polymer powder may be utilized in finely divided form such as, for example, 20 to 250 microns. Admixed with the solid material may be X-ray contrast, polymerization initiator, antibiotics, antiseptic additives, and the like. Conventional X-ray contrast additives such as barium sulphate, zirconium dioxide, zinc oxide, and the like are used in amounts ranging from 5 to 15% w/w. Typical polymerization initiators can be used in amounts ranging from about 0.5 to 3.0% w/w. Examples of such initiators are benzoyl peroxide, lauroyl peroxide, methyl ethyl peroxide, diisopropyl peroxy carbonate. As noted above, the powder component may also contain an antibiotic or antiseptic additive such as aminoglycosides, cephalosporins, macrolides, polymyxin-peptides, tetracyclines, fusidic acid, bacitracin/neomycin. Typically the amount of such additive will be less than 1% based on the weight of the solid polymer or copolymer. Such additives are employed in conventional amounts that range from 0.1 to 2% w/w.

It will be understood that neither the use of most of the aforementioned additives nor the amounts thereof constitute essential features of the present invention. Moreover, the final composition may also containing filler materials such as carbon fibers, glass fibers, silica, alumina, boron fibers, and the like.

The weight ratios of the liquid monomer component and the polymer powder component will range from between 1 to 1.5 and 1 to 2.5, preferably will be about 1 to 2.

As is well known in the art the final bone cement composition is obtained by mixing the liquid monomeric component with the free-flowing, polymeric powder component. The materials are admixed and dispensed in the conventional manner using known equipment.

It is a feature of this invention that the polymer powder component has a glass transition temperature in the range of 37 to 90° C.; while the liquid monomer component, when polymerized, has a glass transition temperature of 23 to 70° C., and where the final bone cement composition has a glass transition temperature in the range of 37 to 70° C. The glass transition temperatures (Tg) are known from literature for all the acrylic homopolymers, see *Polymer Handbook*, J. Brandrup editor, 2nd Edition, John Wiley & Sons N.Y. (1975). For (random) copolymers the Tg can be calculated from the equation:

$$\frac{1}{Tg} = \frac{W_1}{Tg_1} + \frac{W_2}{Tg_2}$$

where the W's are the weight fractions of the monomers in the copolymers and Tg is measured in degrees Kelvin. See for example S. L. Rosen, *Fundamental Principles of Polymeric Materials*, John Wiley & Sons, N.Y. (1982), p. 95. The glass transition temperatures listed here are all cited values or calculated in this way. Expermentally, glass transition temperatures can be determined by DSC, Differentiel Scanning Calorimetri, as well as by other methods.

The invention wil be more fully understood by reference to the following examples:

EXAMPLE I

A series of comparative runs were carried out utilizing a composition falling within the scope of the present invention (Runs 1 and 8), similar compositions with only two of the three monomeric acrylics present (Runs 2, 3 and 4), three compositions using n-buylmethacrylate as the only monomer (corresponds to EPA 0,218,471), (Runs 5, 6 and 7), and a presently available commercial bone cement, CMW-1 from CMW Laboratories, (Run 9). The formulations are specified in Tables A and B. Before mixing, all the cement compounds and molds were condtioned at 23° C. plus/minus 2° C. at least 2 hours prior to testing.

Liquid monomer component was admixed with polymer powder component by stirring with a spatula for 1 minute. The polymer powder component was added to liquid monomer component and stirred with a spatula for 1 minute. The cement was then transferred to the molds. Molds, samples and tests were made in accordance with ASTM F451.

The final bone cement compositions were evaluated and the results are also set forth in Tables A and B. Underlined values indicate undesirable results. The tests as well as the significance of the results are discussed in detail below.

TABLE A

| Formulations | W/W, % | | | |
|---|---|---|---|---|
| Liquid Monomer Component (33.33%) | 1 | 2 | 3 | 4 |
| n-Decylmethacrylate | 30 | 60 | 37.5 | — |
| iso-Bornylmethacrylate | 20 | 40 | — | 28.5 |
| Methylmethacrylate | 50 | — | 62.5 | 71.5 |
| Hydroquinone, ppm | 30 | 30 | 30 | 30 |
| N,N—Dimethyl-p-toluidine* | 0.23 | 0.23 | 0.23 | 0.23 |
| N,N—Hydroxypropyl-p-toluidine* | 0.47 | 0.47 | 0.47 | 0.47 |
| Polymer Powder Component (66.66%) | | | | |
| Poly(butylmethacrylate-co-methylmethacrylate) (40/60) | 90 | 90 | 90 | 90 |
| Barium Sulphate | 10 | 10 | 10 | 10 |
| Benzoyl Peroxide** | 1.4 | 1.4 | 1.4 | 1.4 |
| Properties | | | | |
| Exotherm, °C. | 51 | 33 | 75 | 69 |
| Elasticity Modulus, GPa (Gega Pascals) | | | | |
| 37° C. | 2.3 | 1.2 | 2.3 | 2.65 |
| 23° C. | 2.7 | 2.05 | 2.6 | 2.8 |
| Residual Monomer, % | 0.8 | 0.5 | 0.2 | 1.2 |
| Compressive Strength, MPa (Mega Pascals) | | | | |
| 37° C. | 60 | 27 | 62 | 74 |
| 23° C. | 80 | 42 | 80 | 87 |
| Glass Transistion (Tg) °C. | | | | |
| Liquid Component (when polymerized alone) | 28 | 10 | 13 | 106 |
| Powder Component | 66 | 66 | 66 | 66 |

TABLE A-continued

| Formulations | W/W, % | | | |
|---|---|---|---|---|
| Liquid Monomer Component (33.33%) | 1 | 2 | 3 | 4 |
| Cement Product | 52 | 45 | 46 | 79 |

*percentage of liquid monomer composition
**percentage of polymer powder component

TABLE B

| Formulations | W/W, % | | | | |
|---|---|---|---|---|---|
| Liquid Monomer Component (33.33%) | 5 | 6 | 7 | 8 | 9 |
| n-Decylmethacrylate | — | — | — | 30 | — |
| iso-Bornylmethacrylate | — | — | — | 20 | — |
| Methylmethacrylate | — | — | — | 50 | 100 |
| n-Butylmethacrylate | 100 | 100 | 100 | — | — |
| Hydroquinone, ppm | 30 | 30 | 30 | 30 | 22 |
| N,N—Dimethyl-p-toluidine* | 2.6 | 0.23 | 2.6 | 0.23 | 0.83 |
| N,N—Hydroxypropyl-p-toluidine* | — | 0.47 | — | 0.47 | — |
| Polymer Powder Component (66.66%) | | | | | |
| Poly(ethylmethacrylate) | 90 | 90 | — | 90 | — |
| Poly(butylmethacrylate-co-methylmethacrylate) (40/60) | — | — | 90 | — | — |
| Polymethylmethacrylate | — | — | — | — | 90.6 |
| Barium Sulphate | 10 | 10 | 10 | 10 | 9.4 |
| Benzoyl Peroxide** | 1.4 | 1.4 | 1.4 | 1.4 | 2.8 |
| Properties | | | | | |
| Exotherm, °C. | 56 | 57 | 51 | 58 | 82 |
| E. Modulus, GPA | | | | | |
| 37° C. | 0.9 | 0.9 | 1.2 | 1.9 | 2.8 |
| 23° C. | 1.8 | 1.4 | 1.6 | 2.4 | 3.1 |
| Residual Monomer, % | 0.5 | 0.8 | 0.4 | 0.8 | 2.2 |
| Compressive Strength, MPa | | | | | |
| 37° C. | 21 | 23 | 24 | 49 | 73 |
| 23° C. | 48 | 38 | 36 | 68 | 94 |
| Glass Transistion (Tg), °C. | | | | | |
| Liquid Component (when polymerized alone) | 20 | 20 | 20 | 28 | 105 |
| Powder Component | 65 | 65 | 66 | 65 | 105 |
| Cement Product | 49 | 49 | 49 | 52 | 105 |

*percentage of liquid monomer composition
**percentage of polymer powder component The above data demonstrate that Runs 1 and 8, which are within the scope of the present invention, not only show excellent exotherm and residual monomer characteristics but also have excellent modulus of elasticity and compression strength properties.

As will be noted, the high exotherm that occurs with many presently available bone cements and a number of bone cements which do not utilize the three separate liquid monomeric acrylates of the present invention, can be avoided. More particularly, the exotherm should be less than about 60° C., and preferably less than about 56° C. which is the denaturation point of proteins. Furthermore, a low monomer residual content of about 1% or lower, generally from about 0.5 to 1%, is attained. At the same time, Runs 1 and 8 reveal elasticity modulus and compressive strength characteristics in the desired range. It follows that the bone cement of the invention have a unique balance of highly desirable properties. In contrast, the comparative bone cements, as enumerated in Tables A and B, fail to meet the desirable standards in one or more respects. As noted above, the specific points of failure are shown by underlining in the tables.

In carrying out the foregoing examples 5, 6, and 7 it was found that the use of n-butylmethacrylate had the further disadvantage of having a very bad, unpleasant smell.

The elasticity modulus (Young's modulus) was determined from the compressive stress/strain data. Compressive strength, on the other hand, was measured by following the procedure outlined in ASTM F451 using a Nene M5 test equipment and running at a crosshead speed of 20 mm/min. The tests were conducted both at ASTM F451 standart temperature (23° C. plus/minus 2° C.) and at body temperature (37° C. plus/minus 1° C.). The samples were conditioned 2 hours before testing.

Residual monomer content was determined by conditioning samples in a 37° C. Ringer-lactate solution for 24 hours. Then the samples are removed and extracted with methanol over a 24 hours period before analyzing the methanol-phase for acrylic monomers on a Perkin-Elmer High Performance Liquid Chromatograph.

EXAMPLE II

A further series of illustrative runs was carried out as in Example I, but where powder content was varied. Results follow:

| Formulations | W/W, % | | | |
|---|---|---|---|---|
| Liquid Monomer Component (33.33%) | 10 | 11 | 12 | 13 |
| n-Decylmethacrylate | 30 | 30 | 30 | 30 |
| iso-Bronylmethacrylate | 20 | 20 | 20 | 20 |
| Methylmethacrylate | 50 | 50 | 50 | 50 |
| Hydroquinone, ppm | 30 | 30 | 30 | 30 |
| N,N—Dimethyl-p-toluidine* | 0.25 | 0.25 | 0.25 | 0.25 |
| N,N—Hydroxypropyl-p-toluidine* | 0.50 | 0.50 | 0.50 | 0.50 |
| Polymer Powder Component (66.66%) | | | | |
| Poly(BMA-co-MMA) (20/80) | 90 | | | |
| Poly(BMA-co-MMA) (60/40) | | 90 | | |
| Poly(ST-co-BA) (80/20) | | | 90 | |
| PolyIBMA | | | | 90 |
| Barium Sulphate | 10 | 10 | 10 | 10 |
| Benzoyl Peroxide** | 1.4 | 1.4 | 1.4 | 1.4 |
| Properties | | | | |
| Exotherm, °C. | 49 | 50 | 54 | 54 |
| Elasticity Modulus, GPa | | | | |
| 37° C. | 2.4 | 1.8 | 2.6 | 1.6 |
| 23° C. | 2.7 | 1.9 | 2.8 | 2.0 |
| Residual Monomer, | 0.7 | 0.5 | 0.9 | 0.6 |
| Compressive Strength MPa | | | | |
| 37° C. | 60 | 44 | 61 | 37 |
| 23° C. | 73 | 51 | 70 | 48 |
| Glass Transition (Tg) °C. | | | | |
| Liquid Component | 28 | 28 | 28 | 28 |
| Powder Component | 84 | 49 | 53 | 53 |
| Cement Product | 66 | 45 | 47 | 47 |

Where
*percentage of liquid monomer component
**percentage of polymer powder component
BMA: butylmethacrylate
MMA: methylmethacrylate
ST: styrene
BA: butylacrylate
IBMA: iso-butylmethacrylate It is also important to recognize that the foregoing data demonstrate the importance for the bone cement to have the specified glass transition temperatures.

Although the present invention has been described and exemplified with respect to its preferred embodiment, it will be understood that the invention may be subject to variations and modifiecations without departing from its broader aspects. Moreover, it should be understood that known procedures for mixing the liquid and the free-flowing powder components and for dispersing the resulting admixture into the bone cavity may be employed in the practice of the present invention.

What is claimed is:

1. An acrylate bone cement composition prepared from a liquid monomeric (meth)acrylate component A and a polymer powder component B, wherein component B comprises (meth)acrylate polymers or copolymers or a mixture thereof having a glass transition temperature in the range of 37° C. to 90° C.; wherein component A comprises a mixture of $C_1$-$C_2$ alkyl methacrylate, a straight or long chain (meth)acrylate having a molecular weight of at least 168, selected from the group consisting of ethylhexyl methacrylate, isodecylmethacrylate, n-decylmethacrylate, and laurylmethacrylate, and a cyclic (meth)acrylate having a molecular weight of at least 168, said mixture having a glass transition temperature when polymerized, in the range of 23° C. to 70° C.; whereby, when the liquid monomeric component A is admixed with the polymer component B, the resulting bone cement composition has a glass transition temperature in the range of 37° C. to 70° C.

2. The acrylate bone cement composition of claim 1 wherein the polymer of component B is poly(butylmethacrylate-co-methylmethacrylate).

3. The acrylate bone cement composition of claim 1 wherein the polymer of component B is polyethylmethacrylate.

4. The acrylate bone cement composition of claim 1 wherein the $C_1$-$C_2$ alkyl methacrylate is methylmethacrylate.

5. The acrylate bone cement composition of claim 1 wherein the cyclic methacrylate of component A is selected from the group consisting of iso-bornylmethacrylate, dicyclopentenyloxyethylmethacrylate, 4 tert-butylcyclohexylmethacrylate, and 3,3,5-Trimethylcyclohexylmethacrylate.

6. The acrylate bone cement composition of claim 1 wherein the liquid component A contains a crosslinking agent.

7. The acrylate bone cement composition of claim 1 wherein the initiator in the polymer component B is benzoyl peroxide.

8. The acrylate bone cement composition of claim 1 wherein the activators in the liquid component A are a combination of N,N-Dimethyl-para-toluidine and N,N-hydroxypropyl-para-toluidine.

9. The acrylate bone cement composition of claim 1 wherein the activator is N,N-Dimethylaminophen ethanol or N,N-Diethylaminophenyl acetic acid.

10. An acrylate bone cement composition prepared from a liquid monomeric (meth)acrylate component A and polymer powder component B having a particle size within the range of 20 to 400 microns wherein component B comprises (meth)acrylate polymer or copolymer or a mixture thereof having a glass transition temperature in the range of 37° C. to 90° C.; and wherein Component A comprises a mixture of 20 to 75% by weight of straight of branched chain methacrylate, having a molecular weight of at least 168, is ethylhexylmethacrylate, isodecylmethacrylate, n-decylmethacrylate or laurylmethacrylate, from about 5 to 60% by weight of a cyclic methacrylate having a molecular weight of at least 168, said mixture having a glass transition temperature, when polymerized, in the range of 37° C. to 70° C.; whereby, when the liquid monomer component A is admixed with the polymer component B in a weight ratio of 1 to 2, a bone cement composition having a glass transition temperature in the range of 37° C. to 70° C. is obtained.

11. The acrylate bone cement composition of claim 10 wherein the polymer component B comprises poly(butylmethacrylate-co-methylmethacrylate).

12. The acrylic bone cement composition of claim 10 wherein the polymer component B comprises polyethyl methacrylate.

13. The acrylate bone cement composition of claim 10 wherein the cyclic methacrylate is isobornylmethacrylate.

14. The acrylate bone cement composition of claim 10 wherein component A contains a crosslinking agent.

15. The acrylate bone cement composition of claim 10 wherein component A contains at least one organic activator.

16. The acrylate one cement composition of claim 10 wherein component A contains at least one polymerization inhibitor.

17. The acrylate bone cement composition of claim 11 wherein component B contains a X-ray contrast additive.

18. The acrylate bone cement composition of claim 10 wherein component B contains a peroxide initiator.

* * * * *

UNITED STATES PATENT AND TRADEMARK OFFICE
CERTIFICATE OF CORRECTION

PATENT NO. : 4,910,259

DATED : March 20, 1990

INVENTOR(S) : Ture Kindt-Larsen and Lydia D. Thomsen

It is certified that error appears in the above-identified patent and that said Letters Patent is hereby corrected as shown below:

Column 10, line 12, change to read:

--75% by weight of methylmethacrylate, from about 5 to 40% by weight of straight or branched chain methacry- --

Signed and Sealed this

Ninth Day of March, 1993

*Attest:*

STEPHEN G. KUNIN

*Attesting Officer*  Acting Commissioner of Patents and Trademarks